United States Patent [19]

Hyndman

[11] Patent Number: 4,475,554
[45] Date of Patent: Oct. 9, 1984

[54] NONINVASIVE CONTINUOUS BLOOD PRESSURE METER

[75] Inventor: Barry W. Hyndman, Amsterdam, Netherlands

[73] Assignee: Nederladse Centrale Organisatie Voor Toegepast-Natuurwetenschappelijk Onderzoek, The Hague, Netherlands

[21] Appl. No.: 317,896
[22] PCT Filed: Jun. 5, 1981
[86] PCT No.: PCT/EP81/00063
§ 371 Date: Oct. 28, 1981
§ 102(e) Date: Oct. 28, 1981
[87] PCT Pub. No.: WO81/03606
PCT Pub. Date: Dec. 24, 1981

[30] Foreign Application Priority Data

Jun. 19, 1980 [NL] Netherlands .................. 8003548

[51] Int. Cl.$^3$ ........................................... A61B 5/02
[52] U.S. Cl. .................................. 128/664; 128/667; 128/677
[58] Field of Search ............... 128/664, 666, 667, 672, 128/679, 680, 681, 682, 683, 687, 688

[56] References Cited

U.S. PATENT DOCUMENTS

| | | | |
|---|---|---|---|
| 4,170,226 | 10/1979 | Albainy et al. | 128/681 |
| 4,178,918 | 12/1979 | Cornwell | 128/688 |
| 4,338,950 | 7/1982 | Barlow, Jr. et al. | 128/687 |
| 4,343,314 | 8/1982 | Sramek | 128/680 |

OTHER PUBLICATIONS

Yamakoshi et al., "Indirect Measurement of Instantaneous Arterial BP in the Human Finger by the Vascular Unloading Technique"; *IEEE Trans. on Biomed. Engr.*, vol. BME-27, No. 3, 3-1980, pp. 150-155.
Wesseling et al., "Implementation of the Penaz Method for Measuring Arterial BP in the Finger and First Results of an Evaluation; *Inst. Med. Phys. TNO;* Progress Report 6; 12-1978, pp. 168-173.
Penaz; "Photoelectric Measurement of BP, Volume, and Flow in the Finger"; DIG. of 10th Int'l Conf. on Med. and Biol. Engr., 1973, p. 104.
Kesteloot et al., "Methodology of BP Measurement and Epidemiology of Hypertension"; *ACTA Cardiologica*, T., XXXIII, 1978, 2, pp. 83-87.
Reichenberger et al., "New Optoelectronic System for Monitoring Peripheral Bloodflow"; Proceeding Biocapt., Paris 1975, pp. 253-258.
Francis, "Improved Systolic-Diastolic Pulse Separator"; *Med. and Biol. Engr.*, 1-1974, pp. 105-108.

*Primary Examiner*—Lee S. Cohen
*Assistant Examiner*—Angela D. Sykes
*Attorney, Agent, or Firm*—Cushman, Darby and Cushman

[57] ABSTRACT

A noninvasive continuous blood pressure meter that reproduces the arterial blood pressure waveform, comprising an inflatable flexible finger cuff which incorporates an infrared transmitter and receiver and electronic circuitry connected to the transmitter and receiver and controlling a dynamic compressor. The dynamic compressor comprises a bellows which is compressed by a linear motor electrically activated by the electronics. The bellows is connected to the inflatable cuff by a flexible tube to which is also attached an electronic pressure transducer, in such a way that the hollow spaces of the bellows tubing, electronic pressure transducer, and cuff form one complete closed air-filled space. When the inflatable cuff is wound around the finger and the electronics are properly adjusted, the signal from the electronic pressure transducer will very nearly correspond to instantaneous arterial blood pressure.

9 Claims, 2 Drawing Figures

NONINVASIVE CONTINUOUS BLOOD PRESSURE METER

TECHNICAL FIELD

This invention relates to an instrument for the noninvasive continuous measurement of arterial blood pressure in which the actual blood pressure waveform is reproduced. This is achieved by means of an inflatable flexible finger cuff which incorporates a photoelectric infrared transmitter and receiver, electronic circuitry connected to the transmitter and receiver and controlling an electro-pneumatic transducer which, in turn, is connected to the inflatable cuff by a flexible tube to which is also attached an electronic pressure transducer.

BACKGROUND ART

A similar instrument is known in accordance with the prior art portion of claim 1 (Czechoslovakian Pat. No. 133205).

However, the finger cuff used in that version of the instrument comprises a number of inflatable sacks in a rigid cylinder with light source and sensor mounted in the cylinder in such a way that the light must pass through the sacks as well as through the finger.

In accordance with the prior art, the idea of placing the photoelectric source-sensor pair directly against the skin, under the pressure cuff (made possible with the advent of miniature photoelectric sources and sensors), was put forward in 1975 by Reichenberger et al. (see Proceedings "Colloque International sur les Capteurs Biomedicaux", Paris, 1975, A7.5). Such a cuff was displayed in a demonstration of a valve and compressed air version of the instrument in Leiden, The Netherlands, in 1978 (Wesseling, K. H.: Niet invasieve vingerbloeddrukmeter, Boerhaave Lezingen, Wetenschappelijk rapport afd. Cardiologie, Academisch Ziekenhuis, Leiden, Oct. 6, 1978), and in Eindhoven, The Netherlands, in 1979 (Wesseling, K. H.: Bloeddrukmeting en een prototype vingerbloeddrukmeter, Colloquium Meten en Regelen, Technische Hogeschool Eindhoven, Afd. der Elektrotechniek en Technische Natuurkunde, June 8, 1979).

Such a cuff is virtually a miniaturized version of the conventional sphygmomanometer cuff, but incorporating an infrared light source and sensor. (Infrared light absorption is insensitive to blood oxygen changes or to changes in extravascular fluid volume resulting from the application of the cuff pressure to the finger.) Owing to the direct skin contact with the light source and sensor obtained in this type of cuff design, a much larger plethysmogram (the signal from the photoelectric sensor) can be obtained than with the original Czechoslovakian cuff design. Motion artifact is substantially reduced also as a result of this intimate contact with the finger plus the absence of the inertia (and thus motion relative to the finger) of a rigid cylinder. The cuff fits a large range of adult finger sizes (a smaller cuff is required for children). With this cuff design, the cuff air space is minimized, this being a major determinant of the size of the linear motor used in the present invention. The cuff length is determined by theoretical considerations of the longitudinal distribution of pressure transmitted from the cuff to the arterial wall, as well as, though to a lesser extent, the light source-sensor field pattern. A cuff length of minimally 4 cm allows accurate measurements to be obtained.

Moreover, in that earlier version (Czechoslovakian Pat. No. 133205) the electro-pneumatic transducer consists of an electrically controlled valve which controls the amount of compressed air shunted to the inflatable finger cuff or leaked off into the surrounding air. It has become apparent that this form of electro-pneumatic transducer represents a severely limiting factor in the operation of such an instrument, owing to the necessary presence of a flow constriction in the pneumatic circuit which thereby limits the speed at which the cuff can be inflated and thus the fastest component in the blood pressure that can be reliably tracked by the instrument. Such a restriction particularly degrades the performance of the instrument at higher heart rates and higher pulse pressures, besides severely limiting the maximum allowable length of flexible tubing connecting cuff and instrument thereby restricting the freedom of movement of the subject or patient. However, an even greater drawback of that earlier version is that its operation relies on the availability of a compressed air source. Whether that source be in metal bottle form or a bulky compressor motor, that version of the instrument cannot be considered to be self-contained.

Another instrument is known in accordance with the prior art employing the same underlying principle, but using a hydraulic system (see Yamakoshi et al., IEEE Transactions on Biomedical Engineering, vol. BME-27, no. 3, March 1980, pp. 150–153). However, such a hydraulic system precludes the use of a flexible finger cuff with all its inherent advantages, owing to the required rapid displacement of a significant mass of water from the prime mover to the cuff which would be required for this type of cuff in order to follow the blood pressure waveform. The resonance frequency of such a system is unacceptably low. Moreover, for this application, air is a much safer medium to work with than water, since leakages in the hydraulic system could be extremely hazardous for the patient.

DISCLOSURE OF INVENTION

The present invention as claimed is intended to remedy these drawbacks by pneumatically generating the controlled pressure in the flexible finger cuff by means of a dynamic compressor. Such a dynamic compressor comprises an air-filled bellows whose degree of compression is controlled by a linear motor. This version of electro-pneumatic transducer is almost an order of magnitude faster than the valve and compressed air version. Moreover, the resulting system dynamics are virtually independent of finger size and arterial pressure level, unlike the earlier version, thus considerably simplifying the electronic compensation required. The motor is driven by a power amplifier which forms part of the electronics, the instrument now being a self-contained unit requiring only connection to the electrical mains supply.

BRIEF DESCRIPTION OF DRAWINGS

One way of carrying out the invention is described in detail below with reference to drawings which illustrate only one specific embodiment, in which.

(16) contains the controls "SYSTOLIC" and "DIASTOLIC" for the beat-to-beat digital display of these values.

Figure 2:
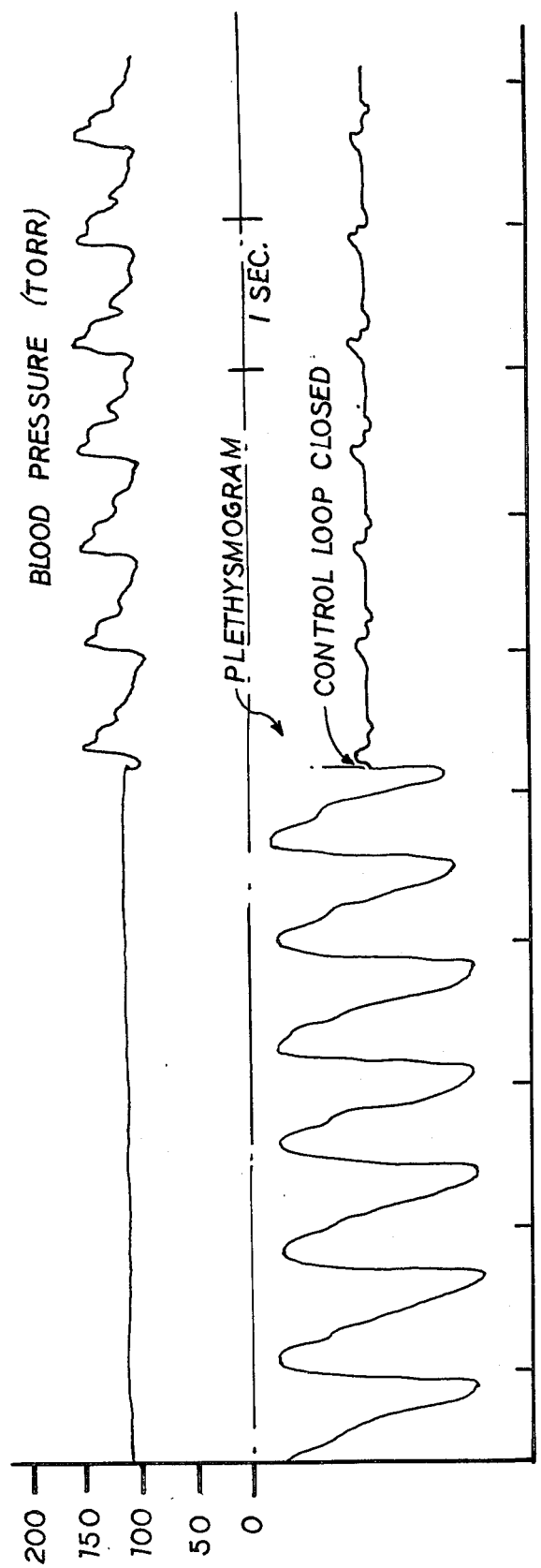

FIG. 2 shows how the instrument clamps the plethysmogram to a fixed (reference) value by producing a cuff pressure, measured by the electronic pressure transducer (15), equal to that in the finger arteries. The reference level corresponds to the d.c. level of the plethysmogram (in open-loop mode) for a cuff pressure which produces a maximum peak-to-peak value in the plethysmogram waveform.

BEST MODE FOR CARRYING OUT THE INVENTION

Figure 1:
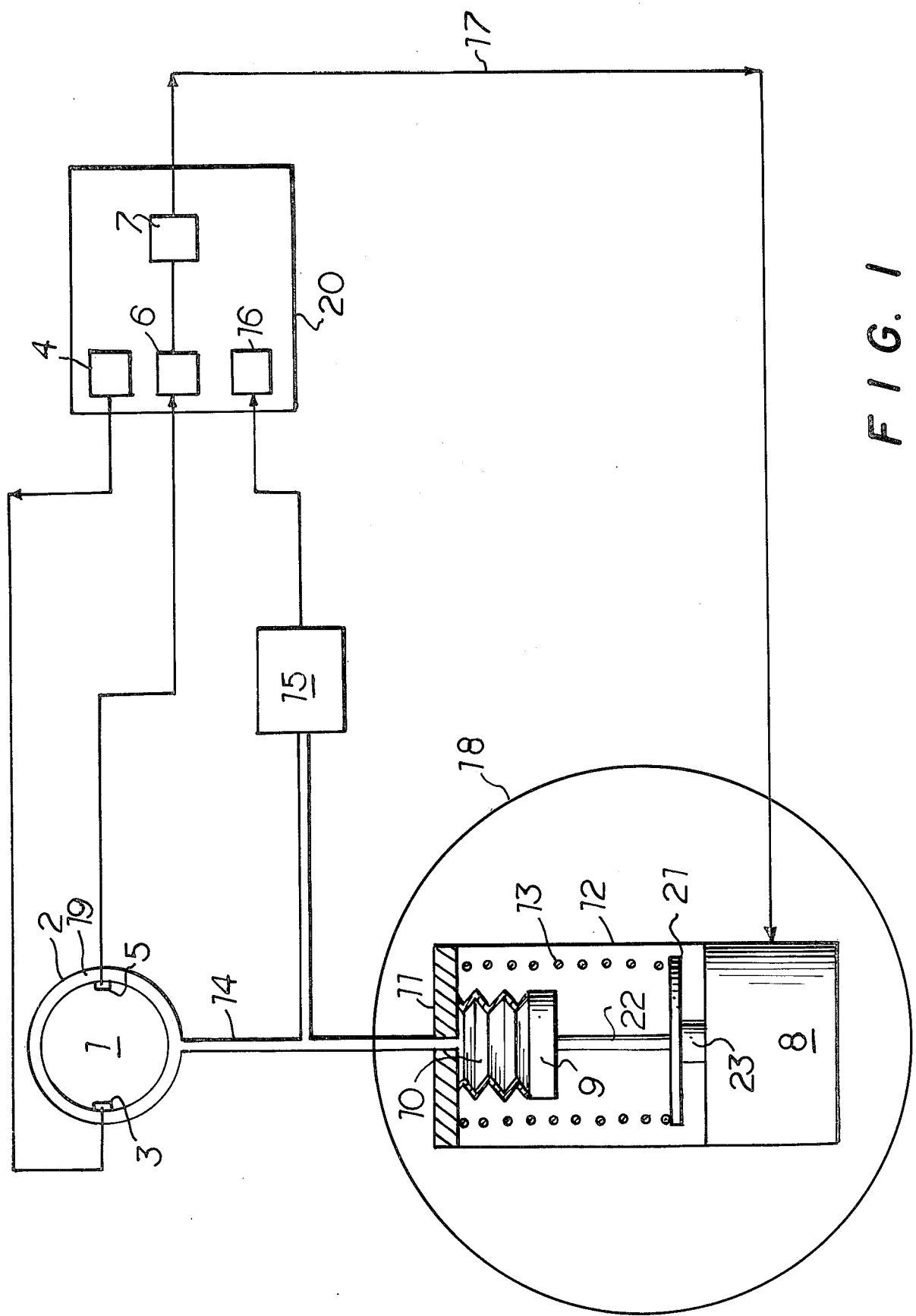
FIG. 1 is a schematic block diagram of the instrument according to the present invention. In addition to the functions described elsewhere in the text, block (7) also incorporates the front panel controls "START", "INITIALIZE", "MEASURE", and "GAIN", while block

The instrument uses the principle of the unloaded vascular wall. As FIG. 1 shows, the finger (1) is surrounded by an inflatable flexible cuff (2). The cuff incorporates an infrared light-emitting diode (LED) (3) which is activated by high frequency electrical impulses from a transmitter circuit (4) and (when the cuff is wound around the finger), located diametrically opposite, an infrared photoelectric sensor diode (5) which receives the resulting impulses of light once they have passed through the finger. Note that the cuff is normally wound around the middle phalanx of the middle finger in such a way that the source and sensor lie against the finger sides. After high-pass filtering (to remove any extraneous disturbances, including mains supply hum and light flicker), the received signal is processed by the demodulator circuit (6), which, after compensation and power amplification (7), activates the linear motor (8). The motor (8), via the plunger (22), controls the position of the plate (9) which is fixed to one end of the bellows (10). The other end of the bellows is fixed to a second plate (11) which, in turn, is mounted on the outer case of the motor by means of four mounting posts (12). In order to utilize the force of traction as well as the force of compression available from the linear motor, three springs (13) are used to link the plate with a plate (21) mounted at the point where the plunger (22) threads into the motor drive spigot (23). In this way, the available uni-directional force of the motor is almost doubled. It should be noted, however, that the power amplifier and its associated power supply used to drive the linear motor must be capable of supplying both positive and negative potential to the motor. The bellows is then connected to the inflatable cuff with flexible tubing (14), to which is also attached an electronic pressure transducer (15), in such a way that the hollow spaces of the bellows, tubing, electronic pressure transducer, and cuff, form one complete closed air-filled space.

The operation of the instrument is then as follows:

The light-emitting diode (3) which is activated by high-frequency electrical impulses from the electronic circuit (4) produces a stream of infrared light impulses. The amplitude of these light impulses, detected by the demodulator circuit (6) from the signal received from the photoelectric sensor diode (5), will only be constant if the walls of the finger arteries under the light beam do not move. It is this state, specifically when this portion of the finger arteries are unstressed (both radially and longitudinally), that one is striving for (see "Initialization" description). The function of the electronics (6) and (7) is to ensure that the electrical signal in the lead (17) which activates the dynamic compressor (18) produces this situation (block (7) includes the initialization circuitry and controls, power amplifier, and the electronic compensation of the finger arteries and dynamic compressor/cuff combination). The necessary consequence of this state prevailing is that the instantaneous cuff pressure is very nearly equal to the pressure in the finger arteries.

The dynamic compressor (18) comprising the the linear motor (8), plunger (22), bellows end-plates (9) and (11), and the bellows (10) which is fixed to the outer case of the motor by the end-plate (11) and the mounting posts (12), generates a pressure in the hollow space (19) of cuff (2) which is measured by the electronic pressure transducer (15). The signal from this transducer is calibrated and the beat-to-beat diastolic and systolic values detected and displayed by the electronic circuitry (16). The springs linking plates (11) and (21) allow the force of traction available from the motor (8) to effectively be transformed into an additional force of compression, thereby almost doubling the available force (and thus pressure) which would otherwise be available.

The dynamic compressor

The dynamic compressor comprises a bellows which is compressed by a linear motor. Such motors are commercially available under the names "shakers", "vibration exciters", and "vibrators". As their names suggest, they are normally used in vibration testing of materials and structures.

The diameter of the bellows was chosen such that a stroke of 0.5 cm (the standard stroke available from most of the smaller range of commercial shakers) could produce a pressure of 300 Torr in the cuff loosely wound around an adult middle finger. (It should be noted that winding the cuff too tightly around the finger will produce incorrect instrument readings due to "preloading" the finger.) Such a bellows has an outer diameter of about 3.5 cm and requires a force of about 4 kg to produce this pressure.

The bellows is constructed in such a way that when it is fully compressed its remaining air space (the dead space) is minimal, since the cuff pressure attainable (in fractions of an atmosphere) is the ratio of the compressor stroke volume to the sum of the cuff volume plus the dead space of the bellows. This can be achieved either by inserting a solid block into the bellows to occupy whatever dead space does exist, or by using a very short bellows constructed of thin material. The latter technique was used in the present version of the instrument.

In order to utilize the force of traction as well as the force of compression available from such commercial shakers, three springs were used to provide an additional force of compression across the bellows. It should be noted from FIG. 1 that the mounting posts (12) and plunger (22) were made long enough that the full motor stroke is a small fraction of this length. In this way the force of the (preloaded) springs does not appreciably change over the full motor stroke, a prerequisite for optimal force transfer. The available uni-directional force of the shaker (and thus attainable cuff pressure) is thereby almost doubled. Thus, a shaker capable of delivering a vector force of at least 2 kg over a distance of 0.5 cm suffices as the prime mover for the system. It should be noted, however, that the power amplifier and its power supply (contained in block (7) of FIG. 1) used to drive the shaker must be capable of supplying both positive and negative potential.

Electronic compensation

The electronic compensation, contained in block (7) of FIG. 1, comprises an integrator (so that changes in mean blood pressure can be accurately followed) combined with a band-limited first-order high-emphasis d.c.-coupled amplifier to compensate for the visco-elastic wall properties of the finger arteries, and a band-limited second-order high-emphasis d.c.-coupled amplifier to compensate for the second-order resonance effect of the compressor-cuff combination (resulting from the moving mass of the motor, the stiffness of its suspension spring, and the compliance of the air-filled bellows and cuff) the parameters of which are obtained from the Bode plot of the compressor-cuff combination. The compressor-cuff combination possesses much faster dynamics than a combination of cuff with a valve and compressed air form of electro-pneumatic transducer, owing to the necessary presence of a flow constriction in the latter which thereby limits the speed at which the cuff can be inflated and thus the fastest blood pressure component that can be reliably tracked. The present form of electro-pneumatic transducer is almost an order of magnitude faster than the earlier version. Moreover, the resulting system dynamics are virtually independent of finger size and arterial pressure level, thus considerably simplifying the electronic compensation required.

The corner frequency of the finger compensator was obtained from the Lissajous figure resulting from the plethysmogram signal on the vertical plates of an oscilloscope and the sinusoidally varied finger cuff pressure on the horizontal plates. This was found to be between 5 and 10 Hz, varying somewhat for different subjects, but within the range reported from actual physiological measurements on the visco-elastic wall properties of systemic arterial segments. In fact, the use of the instrument in this mode of operation, viz., to estimate the visco-elastic time constant of peripheral arteries, may prove to be of clinical value in screening for such diseases as, e.g., arterioscleroses.

Band-limiting (of the high-frequency emphasis) is required in the compensation networks so that the noise intrinsic to the photoelectric sensor diode is not unduly amplified. This would limit the degree to which the plethysmogram could be clamped (the error signal can be no smaller than the noise). The higher the natural resonant frequency of the mechanical pressure generating system, the less electronic high-frequency emphasis required, which limits the noise amplification and thereby allows greater clamping of the plethysmogram to be attained. The spring suspension of the motor must be stiff enough that, when combined with the compliance of the air-filled bellows and cuff, the resonant frequency of the pressure generating system is high enough not to require too much electronic high-frequency emphasis, but still allow a maximum cuff pressure of 300 Torr to be attained. Since the moving mass of the motor combined with only the compliance of the air-filled bellows and cuff already gives an acceptably high resonant frequency, the suspension spring need only be stiff enough to provide adequate mechanical support for the moving mass.

As FIG. 2 shows, this form of compensation allows a high enough loop gain to be attained that the plethysmogram can be clamped to a small fraction of its open-loop pulsation, without the outbreak of large extraneous oscillations which result if such compensation is not included. In fact, the effective accuracy of the instrument in following the finger blood pressure is even higher than that indicated by the (already) small pulsations in the plethysmogram, owing to the fact that, in the unloaded region of the finger arteries, even a small change in transmural pressure results in a relatively large change in arterial cross-section. Thus, a given reduction in plethysmogram pulsation in this region (by closing the control loop) is indicative of an even smaller error between cuff and arterial pressure. This can also be seen from the fact that above a certain level of loop gain ("GAIN" on front panel) (the factor determining the error and thus measured waveform in a feedback control system), further increases in the loop gain do not alter the form of the measured blood pressure signal but only serve to introduce extraneous noise into the signal. The d.c. value to which the plethysmogram is clamped corresponds to the value resulting from an open-loop cuff pressure which produces a maximum peak-to-peak plethysmogram waveform, as explained in the next section.

Adjustment of reference level ("initialization")

The reference level to which the plethysmogram is clamped is determined by the following procedure ("initialization"), the circuitry and controls of which are contained in block (7) of FIG. 1. The feedback loop is opened (press button "INITIALIZE" on front panel), i.e., the dynamic compressor is disconnected from the (compensated) plethysmogram and its driving potential is varied manually by means of a potentiometer on the front panel (also marked "INITIALIZE") until the peak-to-peak amplitude of the plethysmogram (indicated by the front panel digital display) is maximum. (With the abundance of inexpensive microprocessors currently commercially available, this adjustment can be reduced to a push-button operation.) The "reference adjust" circuit automatically adjusts to the d.c. value of the plethysmogram and this value is stored and used as the reference value when the loop is again closed (press button "MEASURE"). It can be shown that the diameter of the finger arteries will now be maintained at a value corresponding to their unloaded region. FIG. 2 shows that when the loop is closed, any deviations in intravascular volume due to changes in intravascular pressure are immediately compensated by an automatic adjustment of cuff pressure which therefore instantaneously follows the intravascular waveform. That the value to which the plethysmogram is clamped corresponds to the unloaded region of an artery can be seen (in the closed-loop mode) when the reference level is made to slowly decrease linearly with time. A plateau is obtained in the cuff pressure-plethysmogram relationship, characteristic of the unloaded region of an artery. The range of reference level values corresponding to this plateau is equal to the range of d.c. values of the plethysmogram which occur when the cuff pressure (open-loop mode) is adjusted to give maximum peak-to-peak plethysmogram waveforms.

Finger height correction

Unless the subject is lying down, the blood pressure in the finger differs substantially from that measured by a conventional sphygmamanometer or a catheter in the brachial artery, owing to the hydrostatic pressure differential between heart and finger. This hydrostatic differential can be corrected for in the instrument by fastening a small external electronic pressure transducer to the patient at heart level (e.g., by placing it in a shirt pocket over the heart) and connecting this transducer to a thin water-filled flexible tube which runs to the measured finger, taped at intervals along the arm. At the finger the tube is sealed with a thin compliant membrane. The electrical signal from this transducer is then electronically added to that of the internal (cuff pressure) transducer and the resulting signal corresponds to finger blood pressure corrected to heart level.

Leak correction

When the instrument is about to be used, the power is switched on and the operator pushes the button marked "START" which opens an on-off air valve (not shown in FIG. 1) in the normally closed pneumatic circuit as well as causing the drive spigot of the linear motor to fully retract. The cuff is then wound around the finger and the button marked "INITIALIZE" is pressed which closes the valve and disconnects the dynamic compressor from the (compensated) plethysmogram, leaving it connected only to a potentiometer-controlled voltage. The operator then turns the potentiometer knob (also marked "INITIALIZE"), until the digital display shows a maximum. (As already mentioned, this initialize procedure can be automated to a push-button operation with the aid of a small microprocessor.) Finally, by pushing the button marked "MEASURE", the control loop is closed, i.e., the dynamic compressor is again connected to the (compensated) plethysmogram, the d.c. value of which has been made zero by the reference adjust circuit, and the pressure transducer will measure arterial blood pressure. Should there be a slow leak in the pneumatic system the drive spigot of the motor will gradually move forward in order to nonetheless clamp the plethysmogram to zero. However, when the drive spigot finally reaches its maximum outward displacement (as sensed by a limit switch), the electronics produce a situation equivalent to that of pressing "START", viz., the air valve is opened and the drive spigot fully retracts for sufficient time to replenish the system with the air that has leaked out, after which time the valve is again automatically closed and the instrument is again automatically returned to the "MEASURE" mode. In the normal course of events, this should only occur about once an hour and require only a few seconds.

I claim:

1. An instrument for continuously and non-invasively measuring the absolute arterial blood pressure of a subject, in which the entire arterial blood pressure waveform is reproduced, comprising:
   a wrap-on flexible finger cuff having an inflatable portion which incorporates a photoelectric plethysmogram underneath said inflatable portion of the cuff and including an infrared transmitter and infrared receiver located such that they will be on opposite sides of a finger about which the cuff is wrapped,
   an electro-pneumatic transducer which incorporates an air-filled compressible space pneumatically connected to the inflatable cuff by flexible tubing such that the inflatable portion of the cuff, compressible space, tubing and transducer form one complete closed air-filled space,
   electronic circuit means connected to the infrared transmitter, receiver, and electro-pneumatic transducer for generating said blood pressure waveform and a control signal; and
   means, responsive to said control signal, for varying the volume of the compressible space of the electro-pneumatic transducer fast enough to keep the instantaneous value of a plethysmogram signal of said plethysmograph close to a predetermined fixed reference value.

2. An instrument according to claim 1, wherein said electronic circuit means incorporates an electronic compensation network connecting the photoelectric plethysmograph to a power amplifier which compensates for the mechanical properties of the transducer and cuff as well as the visco-elasticity of the arterial wall segments underneath the finger cuff.

3. An instrument according to claim 1, wherein the fixed reference value corresponds to an unloaded region of the arteries underneath the finger cuff.

4. An instrument according to claim 1, further comprising an additional pressure transducer adapted to be located at the subject's heart level and means for electronically adding an electrical signal from the electro-pneumatic transducer to an electrical signal from the additional pressure transducer adapted to be located at the heart level of said subject, said additional pressure transducer being connected to a water-filled flexible tube running to the finger about which the cuff is wrapped where it is sealed with a compliant membrane.

5. A blood pressure measuring device for producing a complete arterial blood pressure waveform, comprising:
   a wrap-on inflatable flexible finger cuff having a hollow portion;
   a photoelectric plethysmograph including an infrared transmitter and receiver attached to said finger cuff such that when said cuff is wrapped about a finger of a subject, the transmitter and receiver will be on opposite sides of the finger;
   a pressure transducer which generates a transducer signal indicative of pressure in the hollow portion of said finger cuff, said pressure signal indicated being of a complete arterial blood pressure waveform;
   control means for (a) providing a drive signal to said transmitter, (b) receiving and processing a signal from said receiver, (c) receiving and processing said transducer signal, and (d) generating a control signal; and
   compressible air space servocontroller pressurizing means for controlling the pressurization of said cuff responsive to said control signal, the cuff, plethysmograph and control means forming a closed loop control system for regulating the cuff pressure sufficiently rapidly to maintain the signal from the receiver within a predetermined range.

6. A blood pressure measuring device according to claim 5 wherein said control means comprises means for compensating for mechanical properties of said pressurization control means, cuff and for the visco-elasticity of arterial wall segments within said finger.

7. A blood pressure measuring device according to claim 5 wherein the predetermined range corresponds to an unloaded region of finger arteries within the cuff.

8. A blood pressure measuring device according to claim 5 further comprising a second pressure transducer adapted to be placed at a subject's heart level and means for electronically adding the signals of said pressure transducer and said second pressure transducer, the second transducer being coupled to a water-filled flexible tube running to the finger about which the cuff is wrapped where it is sealed with a compliant membrane.

9. A blood pressure measuring device according to claim 5 wherein said compressible air space servocontroller pressurizing means comprises:
 a linear motor driven by said control signal;
 a first plate;
 a plunger coupling said first plate to said linear motor;
 a bellows having a first end coupled to said first plate and a second end;
 a second plate coupled to said second end of said bellows;
 a casing to which said motor and second plate are fixed; and
 a flexible tube which couples said bellows to said cuff.

* * * * *